US005971756A

United States Patent [19]
Fjelstad

[11] Patent Number: 5,971,756
[45] Date of Patent: Oct. 26, 1999

[54] METHOD AND APPARATUS FOR CREATING PATTERNS FOR DENTURES

[76] Inventor: Harold K. Fjelstad, 6616 Fourth Ave. South, Minneapolis, Minn. 55423-2420

[21] Appl. No.: 09/072,440

[22] Filed: May 4, 1998

Related U.S. Application Data

[63] Continuation-in-part of application No. 08/627,886, Apr. 3, 1996, Pat. No. 5,810,586.

[51] Int. Cl.⁶ .................................................. A61C 19/04
[52] U.S. Cl. ................................ 433/68; 433/69; 433/72; 433/73
[58] Field of Search ........................... 433/69, 68, 71, 433/73, 214, 213, 72

[56] References Cited

U.S. PATENT DOCUMENTS

| | | | |
|---|---|---|---|
| 1,589,802 | 6/1926 | Gould | 433/73 |
| 1,589,973 | 6/1926 | Landa | 433/73 |
| 1,662,670 | 3/1928 | Harter | 433/73 |
| 1,786,915 | 12/1930 | McLean | 433/73 |
| 1,864,804 | 6/1932 | Clark | 433/73 |
| 1,944,601 | 1/1934 | Gulic | 33/513 |
| 1,976,045 | 10/1934 | Sorenson | 433/68 |
| 2,017,502 | 10/1935 | Keller | 433/56 |
| 2,107,534 | 2/1938 | Houser | 33/513 |
| 2,154,148 | 4/1939 | Butts | 33/513 |
| 2,461,207 | 2/1949 | Frowine | 433/73 |
| 2,566,903 | 9/1951 | Moran | 433/68 |
| 2,574,427 | 11/1951 | Tully | 33/513 |
| 2,832,137 | 4/1958 | Moore et al. | 433/73 |
| 2,841,871 | 7/1958 | Miller | 433/68 |
| 3,069,774 | 12/1962 | Levey et al. | 433/73 |
| 3,078,584 | 2/1963 | Cohn | 33/514 |
| 3,084,438 | 4/1963 | Goodfriend | 433/73 |
| 3,200,497 | 8/1965 | Goodfriend | 433/44 |
| 3,382,581 | 5/1968 | Balazs | 433/73 |
| 3,452,439 | 7/1969 | Lee | 433/55 |
| 3,464,111 | 9/1969 | Gillard | 433/171 |
| 3,464,115 | 9/1969 | Baker | 433/73 |
| 3,614,950 | 10/1971 | Rabey | 33/514 |
| 3,854,208 | 12/1974 | Arant | 433/73 |
| 3,896,550 | 7/1975 | Lee | 433/57 |
| 3,896,551 | 7/1975 | Stuart | 433/55 |
| 4,096,637 | 6/1978 | Stade | 33/174 |
| 4,126,938 | 11/1978 | Lee | 433/69 |
| 4,261,696 | 4/1981 | Hobo | 433/73 |
| 4,330,277 | 5/1982 | Beu | 433/73 |
| 4,345,898 | 8/1982 | Mack | 433/73 |
| 4,537,574 | 8/1985 | Clark | 433/69 |
| 4,561,846 | 12/1985 | Polizzotto | 433/73 |
| 4,616,998 | 10/1986 | Wong | 433/73 |
| 4,639,220 | 1/1987 | Nara et al. | 433/69 |
| 4,681,539 | 7/1987 | Knap | 433/73 |
| 4,695,252 | 9/1987 | Edwardson | 433/73 |
| 4,836,779 | 6/1989 | Beu | 433/73 |
| 4,843,720 | 7/1989 | Kim | 33/812 |
| 4,932,867 | 6/1990 | Ueno | 433/69 |
| 5,090,901 | 2/1992 | Levandoski | 433/56 |
| 5,154,609 | 10/1992 | George | 433/68 |

OTHER PUBLICATIONS

A.A. Grant & W. Johnson, Ch 9. Principles of Registering Jaw Relationships in An Introduction to Removeable Dentures, 1983.

S. Winkler & L. R. Bailey, Ch 11. Recording Edentulous Jaw Relationships in Essentials of Complete Dentures, Prosthodontics, 1983.

*Primary Examiner*—John J. Wilson
*Attorney, Agent, or Firm*—Patterson & Keough, P.A.

[57] ABSTRACT

This invention consists of a method and apparatus which establish specific central and vertical dimensions and positions for patterns for the making of dentures which will provide a natural occlusion upon replacement of natural teeth.

13 Claims, 7 Drawing Sheets

METHOD AND APPARATUS FOR CREATING PATTERNS FOR DENTURES

CROSS REFERENCES TO RELATED APPLICATIONS

This application is a continuation-in-part of U.S. application Ser. No. 08/627,886, filed Apr. 3, 1996, now U.S. Pat. No. 5,810,586.

FIELD OF THE INVENTION

The invention relates to replacement dentures and, in particular, the invention relates to methods of making dental patterns and devices determining relative positions of patterns for dentures for replacing natural teeth.

BACKGROUND OF THE INVENTION

There has been a long and intensive development of various methods and devices to determine the placement of upper and lower dentures and their relative positions in the patient's oral cavity, so as to restore a natural occlusion. This is evidenced by the large number of patents issued for this purpose over a lengthy period of time. The endeavor in this field has been to establish specific reference points relative to the positions of the teeth in the upper and lower jaws. These reference points establish exact positions of patterns for replacing natural teeth with dentures, whereby a natural bite or occlusion is restored.

Many of the devices described in prior art patents are too complex to be practical or do not provide the degree of accuracy required. A major shortcoming has been the inability to provide stable reference points which can be accurately ascertained, especially after all natural teeth have been extracted.

Ear openings with lip support have been used to establish reference points, for example, in U.S. Pat. Nos. 5,090,901 and 3,464,115. With these reference points, any particular position for the placement of dentures is difficult to reproduce, particularly in vertical spacing or dimensioning.

A frame supported on the patient's ears has been used for this purpose. The frame is a transverse rod supported on the bridge of a patient's nose. A lower frame is attached to the lower jaw and a stylus is used with a recording plate to obtain measurements. Such a device is so complex that its use is discouraged.

These and further examples of the prior art are found in U.S. Pat. Nos. 4,836,779; 4,695,252; 4,096,637; and 4,126,938.

The invention herein, as will be described, represents significant improvement and simplicity for establishing a natural bite in dentures.

SUMMARY OF THE INVENTION

A specific object of the invention is to establish specific references or oral dimensions relative to natural teeth, these references are precisely ascertained for the placement of dentures and survive the extraction of the natural teeth.

It is also an object to provide a method and apparatus for precisely making patterns which replicate the relationships of the upper teeth to the maxilla and the lower teeth to the mandible in a closed mouth.

It is another object to provide a method and apparatus to position patterns for dentures in the same place in the mouth as occupied by the natural replaced teeth. The method and use of the apparatus will result in a bite to which the patient has been accustomed, thus eliminating a breaking-in period otherwise required to re-establish a natural occlusion.

It is a further object to simplify the procedure for the exact replacement of natural teeth by dentures.

It is still a further object to provide a method and apparatus for measuring and tracking resorption in the residual ridges by the equipment disclosed herein.

These and other objects and advantages on the invention will be set forth in the following description in connection with the accompanying drawings in which like reference characters refer to similar parts throughout the several views.

DETAILED DESCRIPTION

The method herein, together with its attendant registration apparatus or device, is described. The method discloses the specific steps undertaken to make patterns and ascertain precise positions of the patterns in the mouth of a patient for both upper and lower replacement dentures. The patterns are then utilized in an articulator where the dentures are made. The dentures, when made by using the present method and apparatus or other device, replicate essential oral dimensions by using references measured by the apparatus prior to tooth extraction. One element of teaching herein is establishing vertical (occlusal) references.

Figure 1:
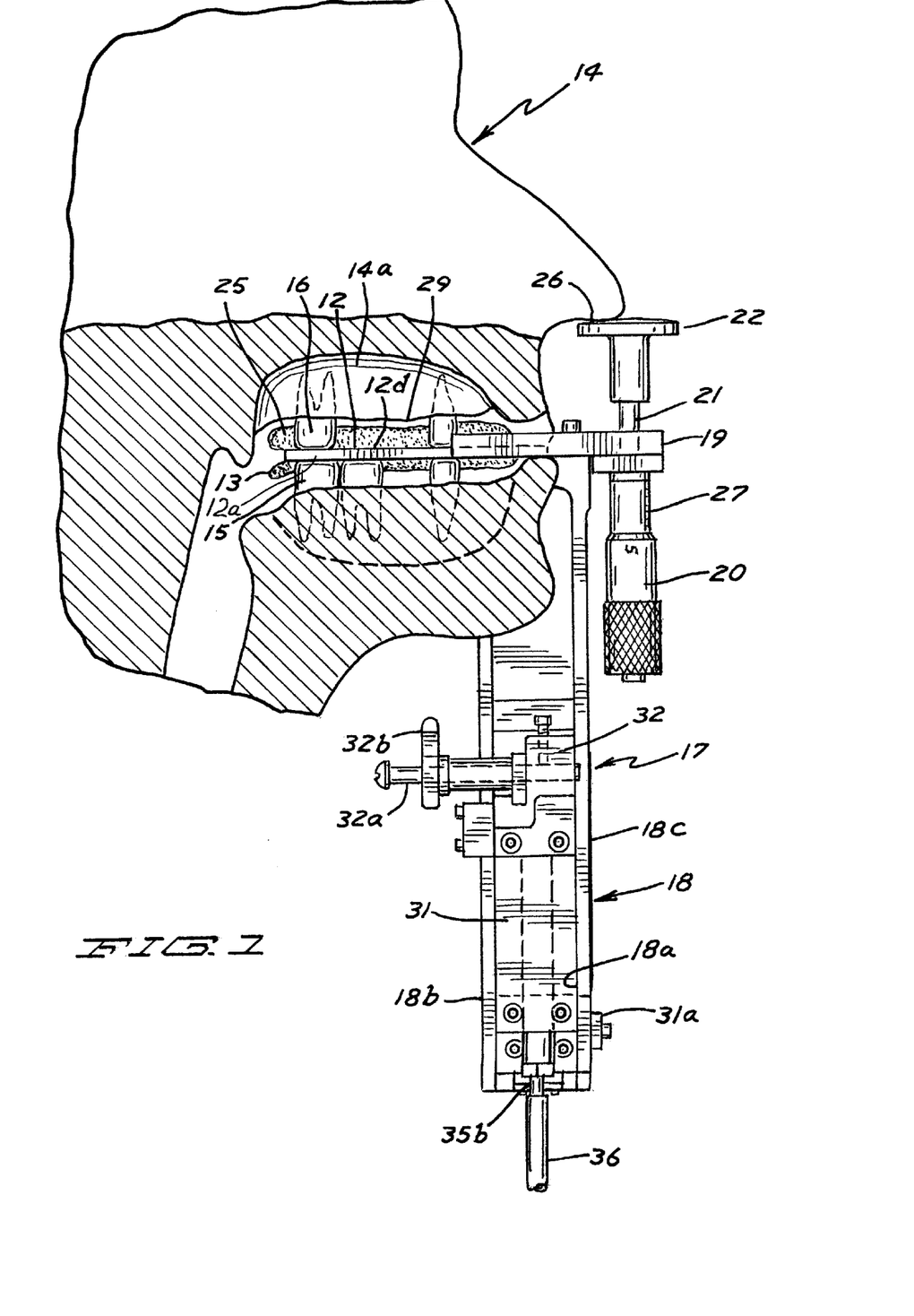
FIG. 1 is a side elevational view of a denture pattern registration device and bite plate, partially in dotted line, in a first operating position.
Figure 2:
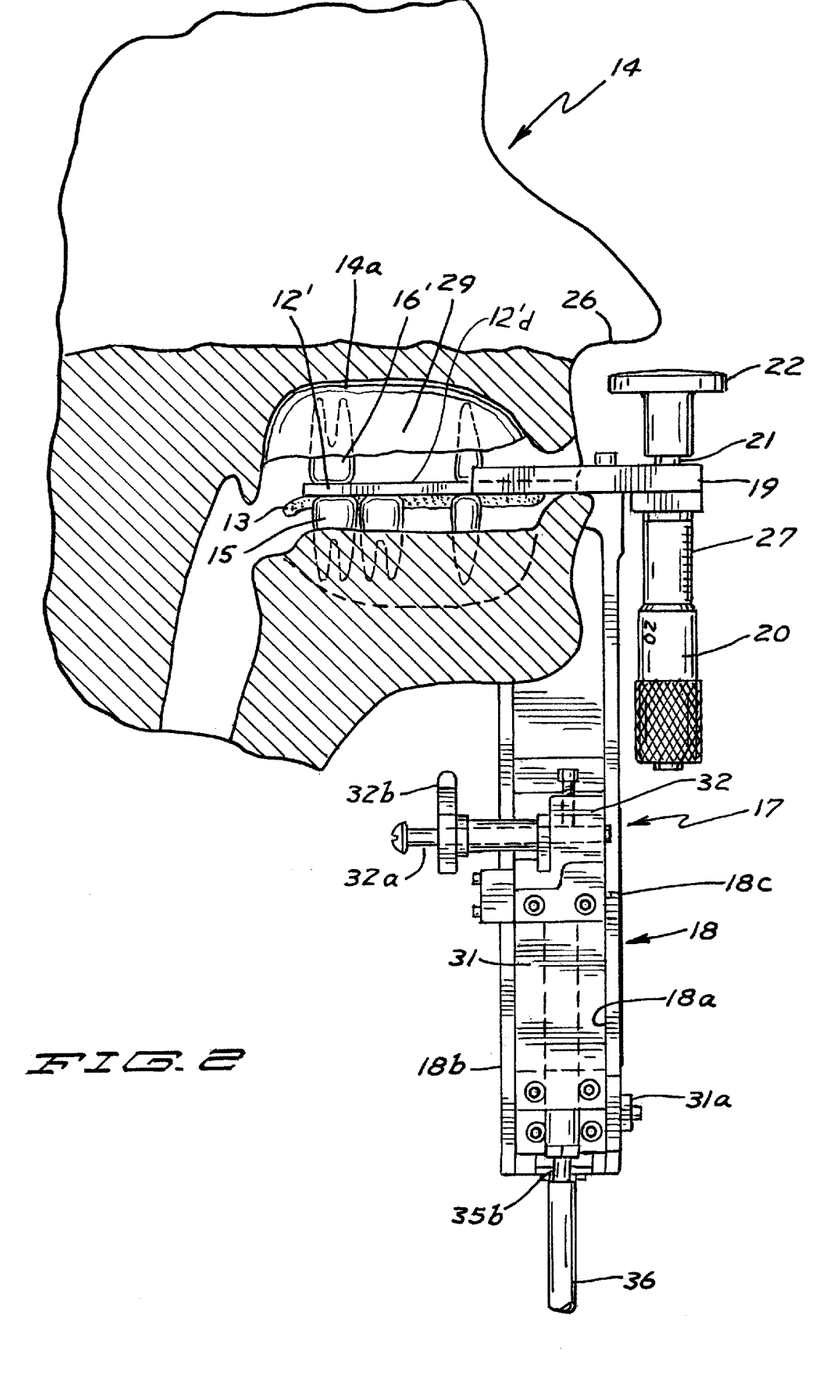
FIG. 2 is a view similar to that of FIG. 1 of a second operating position.
Figure 6:
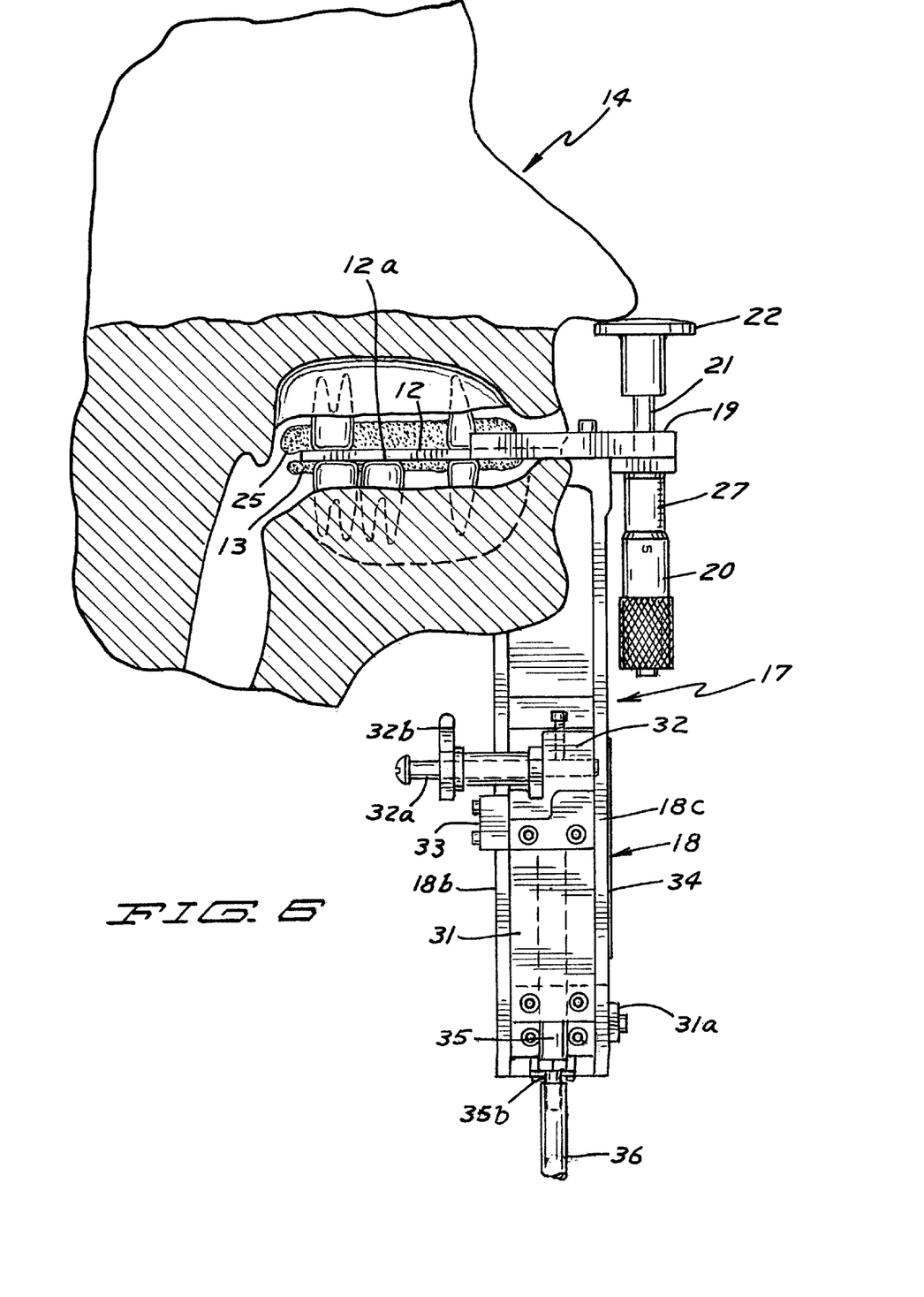
FIG. 6 is a view similar to that of FIG. 1, of the device of FIG. 1 in a related operating position.

Referring to FIGS. 1 and 6, an initial step in making a pattern for an upper denture is to apply a layer of impressionable material 13, such as softened wax, to lower surface 12a of an impressioning member such as bite plate 12. Bite plate 12 is inserted into the mouth 14a of the patient 14 and carefully positioned over lower teeth 15. The patient bites firmly upon bite plate 12 until lower teeth 15 extend through wax layer 13 and contact bite plate 12. At least three lower teeth 15 should penetrate wax layer 13 and contact bite plate 12 in order for bite plate 12 to seat solidly on lower teeth 15 and have a direct relation to the vertical movement of the lower jaw or mandible.

If a third tooth impression has not penetrated wax layer 13 to bite plate 12, a tooth impression (not shown) is selected. The bottom of the tooth impression is cleared of wax to bite plate 12. The cleared impression is refilled with a quick-setting material, such as Denta Stone, to a height sufficient for tooth engagement. Bite plate 12 is then reinserted into the patient's mouth 14*a* in the same location to complete the third tooth impression. Bite plate 12, upon removal from the mouth 14*a*, then has an impression of at least three lower teeth 15 in wax layer 13.

Preparing bite plate 12 to make a pattern is a procedure known in the art. The novelty herein, as will be described, is in establishing references for positioning patterns in the patient's closed mouth 14*a* to provide the same occlusion provided by the patient's natural teeth.

Next, a reference will be established by measuring the position of bite plate 12 in the patient's closed mouth 14*a* as bite plate 12 contacts the patient's upper teeth 15. For this purpose exemplary registration device 17 is used. The function of registration device 17 is to determine and fix a reference (or position) for an upper and lower denture in the patient's closed mouth 14*a*. Exemplary registration device 17 broadly includes an impressioning member and a vertical referencing assembly. The vertical referencing assembly, in turn, includes means for measuring vertical relationships between a biting surface on at least one tooth and an anatomical feature of the patient.

Using registration device 17 enables patterns for upper and a lower dentures to be created. The patterns precisely represent the same positions occupied by the natural teeth prior to extraction. Thus, the pattern, when mounted in an articulator, replicates the same relative positions occupied by the natural teeth prior to extraction. Dentures made from these patterns will have the same occlusion as the natural teeth from which the patterns were made.

With reference to FIGS. 1, 3, 6, 8, and 9, registration device 17 is used to determine the position of an upper denture pattern by means of bite plate 12 and an upper registration assembly of registration device 17 described below. Registration device 17 includes vertically disposed, U-shaped channel member 18 and bite plate holding member 19. Channel member 18 is mounted at a right angle to bite plate holding member 19. Bite plate holding member 19 defines a pair of opposed slots 19*a*, 19*b*, which accommodate bite plate 12.

Holding member 19 has mounted thereon a distance measuring means, such as micrometer 20. Micrometer 20 includes upwardly extending spindle 21 and disc wheel 22. Disc wheel 22 is affixed to the upper end of spindle 21 and is elevated or lowered when micrometer 20 is operated.

Referring to FIG. 1, registration device 17 has mounted therein bite plate 12. The impression of lower teeth 15 in wax layer 13 is present on lower surface 12*a* of bite plate 12. A coat of mold-forming impressionable material 25 (such as Alginate or an equivalent) is poured over upper surface 12*d* of bite plate 12 to about the thickness of a tooth height. With this coating applied, bite plate 12 is inserted into the mouth 14*a* of the patient and positioned on lower teeth 15. Bite plate 12 and the coating are moved upwardly when the patient's mouth 14*a* is closed, thereby inserting upper teeth 16 into the coating. Bite plate 12 is held carefully in this position until impressionable material 25 hardens. In the meantime, micrometer 20 is operated to raise disc wheel 22 until base 26 of the patient's nose is engaged without pressure. A micrometer reading 27 is recorded. Micrometer reading 27 will be used to establish the first vertical reference dimension in the pattern after upper teeth 16 are extracted and underlying gums are healed. At this time, centric and lateral positions of the upper teeth, relative to the lower teeth, have also been established. Bite plate 12 is removed from the patient's mouth 14*a* and upper teeth 16 may be extracted. It is noted that the position of device 17 is determined by the placement of bite plate 12 in the mouth 14*a* of the patient.

Bite plate 12 now has an open-faced mold 23 formed on upper surface 12*d*. Mold 23 records and replicates the arrangement and location of upper teeth 16 relative to the upper, healed gum.

Figure 9:
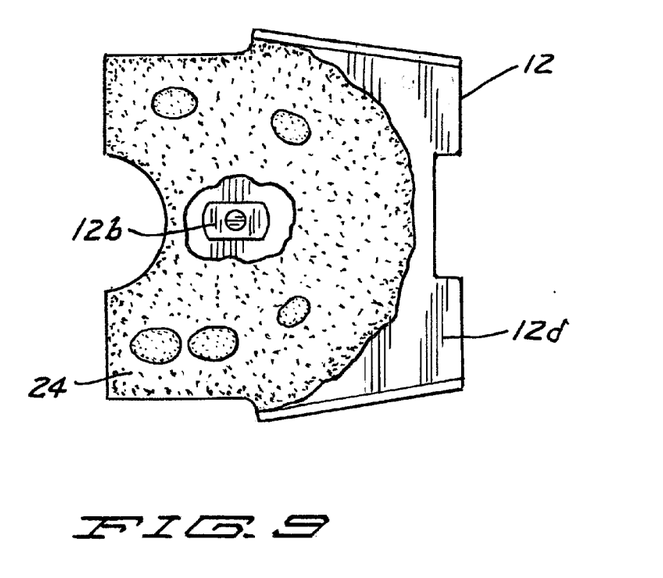
FIG. 9 is a top plan view of the bite plate of FIG. 8, held by the device of FIG. 1.

As shown in FIG. 9, a cast-forming material, such as Denta Stone, is poured into mold 23 to a depth of about the height of a tooth and allowed to overflow onto bite plate 12 around anchor nut 12*b* and into recess location holes 12*c*. This practice is known in the art and is not shown. After the cast-forming material has set, cast 24 is formed. Cast 24 may be detached from bite plate 12 to remove underlying impressionable material from bite plate 12. Cast 24 may then be reattached to bite plate 12, as depicted in FIG. 9. When the patient's upper gum 29 has healed, the following steps are taken:

Bite plate 12 is again inserted into bite plate holding member 19. Cast 24, on bite plate 12, then functions as a tray for holding impressionable material, such as softened wax. Another layer 13 of softened wax is applied to cast 24 at a depth or thickness of a tooth height, usually about 7–8 mm. Bite plate 12 is again carefully inserted into the patient's mouth 14*a* and positioned with the previous underside wax impression on lower teeth 15. Micrometer 20 is reset to the previous micrometer reading 27.

The patient's healed upper gum closes down upon bite plate 12 and into layer 13 in cast 24 until disc wheel 22 contacts base 26 of the patient's nose. The pressure of the upper gum squeezes out excess impressionable material. Cast 24, with the impressionable material thereon, is thusly positioned in the same central location and vertical dimension in the mouth 14*a* as when the first vertical reference point was established. Thus, there is provided a pattern for an upper denture. The pattern records and replicates the precise location of each natural tooth. The pattern further records the vertical relation of each extracted tooth relative to the healed gum.

Figures 3, 4, 5:
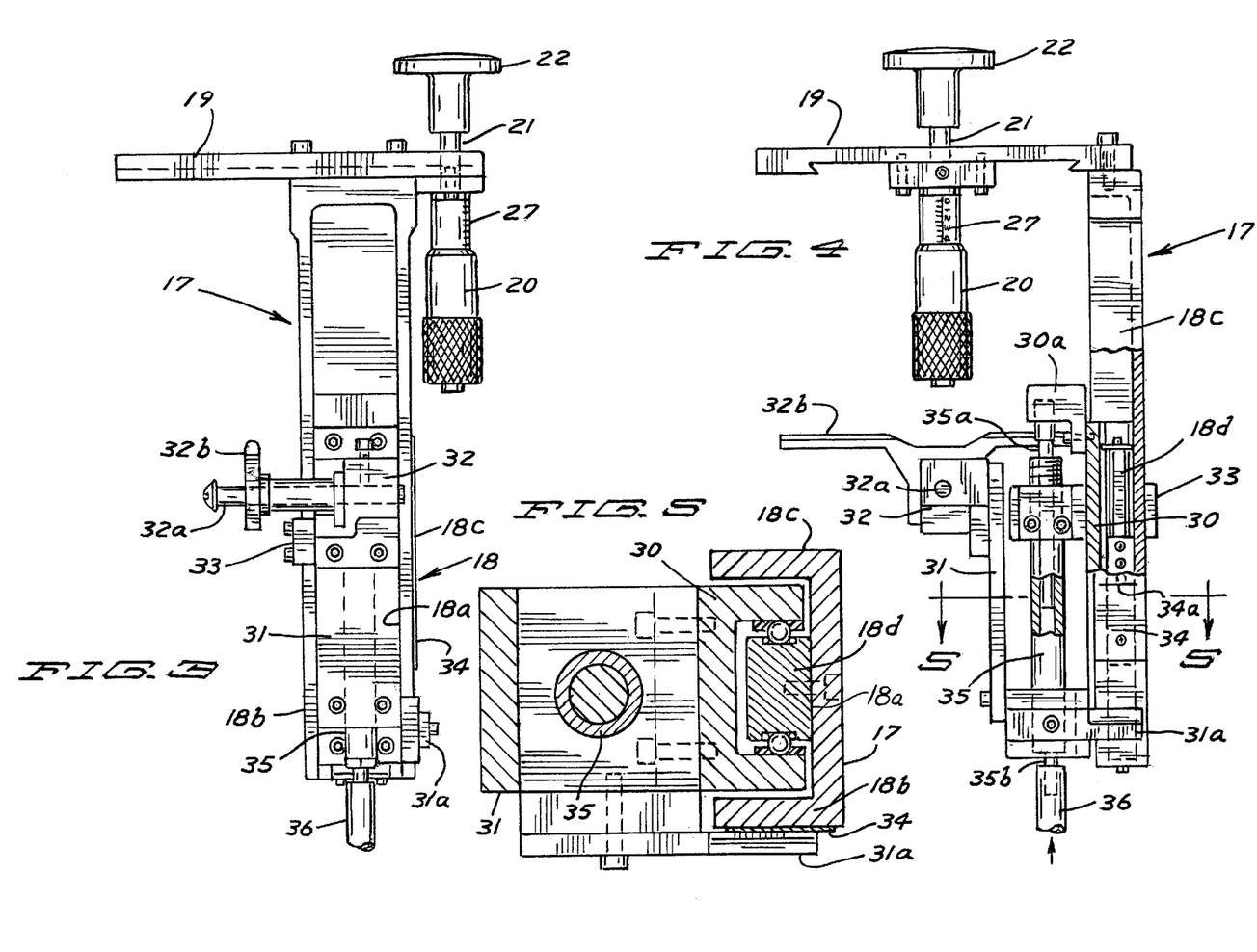
FIG. 3 is a side elevational view of the device of FIG. 1.
FIG. 4 is a rear elevational view of the device of FIG. 1.
FIG. 5 is a sectional view of the device of FIG. 1, taken along line 5—5 of FIG. 4.

Referring to FIGS. 3–5, the function of registration device 17 with regard to making a lower denture pattern is described by means of bite plate 12 and a lower registration assembly of registration device 17 as described below. Registration device 17 as indicated, includes channel member 18 with sidewalls 18*b* and 18*c*. Sidewalls 18*b* and 18*c* define channel 18*a*. Rail 18*d* is affixed in channel 18*a*. Ball slide 30 is mounted on rail 18*d* by means of elongated vertical, angled bracket 31. Bracket 31 includes arm 31*a*, which slides along side wall 18*c*. Removable marking strip or sticker 34 is removably affixed to side wall 18*c* and is discussed below.

Also mounted on bracket 31 is bracket 32. Bracket 32 includes rotatable and outwardly projecting shaft 32*a*. Shoulder bracket 32*b* extends from shaft 32*a*.

Bracket 33 is carried by side wall 18*b*. Bracket 33 angles upwardly to extend over ball slide 30. Air cylinder 35 is carried by bracket 33. Air cylinder 35 overlies and extends longitudinally from ball slide 30. Air cylinder 35 includes rod 35*a*. Rod 35*a* is projected by air pressure from tube 36. Tube 36 connects a controlled air supply (not shown) to inlet 35*b* of air cylinder 35. End wall 30*a*, at the upper end of ball slide 30, is displaced by a projection of rod 35*a* as will be further described.

Figure 7:
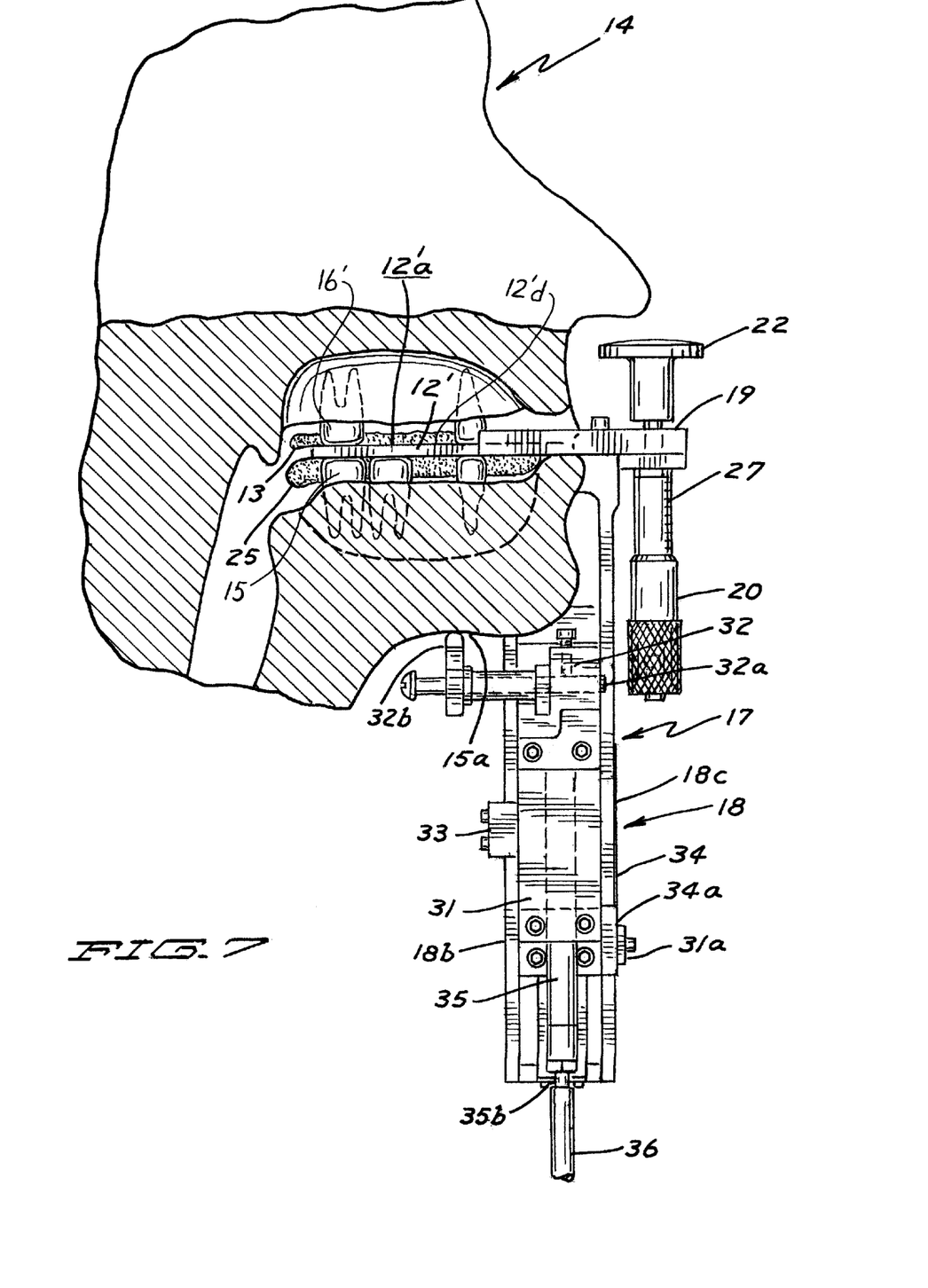
FIG. 7 is a view similar to that of FIG. 2, showing the device of FIG. 1 in a related operating position.
Figure 8:
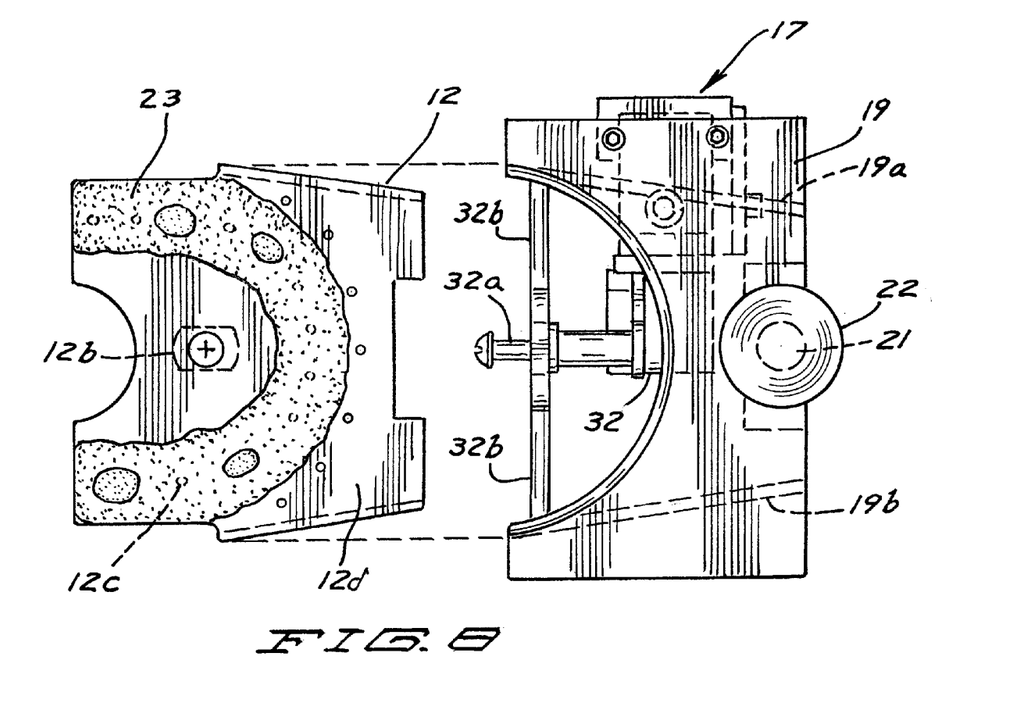
FIG. 8 is a fragmentary top plan view of the device of FIG. 1, showing a portion thereof in dotted line and the extension of a bite place held thereby.

Referring to FIG. 7 and prior to the use of registration device 17, as relating to a pattern for a lower denture and in keeping with the description of a pattern for an upper denture, a bite plate, hereafter 12', is coated on its upper surface 12'd with a layer of softened impressionable material 13, such as wax, to a depth on the order of 3–4 mm. Bite plate 12' and wax layer 13 are carefully positioned in the patient's mouth 14a. The patient then bites down through wax layer 13 until the patient's upper teeth contact bite plate 12', thereby establishing an impression of the upper teeth, which at this point have been replaced by new upper denture 16'. This is the same procedure as previously practiced with bite plate 12 on its reverse side, but using upper denture 16' instead.

Bite plate 12' is then removed from the patient's mouth 14a and mounted into bite plate holding member 19. Bite plate 12', thus attached, is reinserted into the patient's mouth 14a to be held against upper denture 16'. While thus held, air cylinder 35 is charged with pressurized air, causing rod 35a to extend. Shoulder bracket 32b is thereby projected upwardly until lower jaw 15a is engaged. Shoulder bracket 32b continues to engage lower jaw 15 as the patient's mouth 14a is closed. The air pressure which actuates air cylinder 35 rises to a predetermined pressure level (such as 15 psi) to maintain sufficient contact between shoulder bracket 32b and lower jaw 15a. With lower jaw 15a fully closed, line 34a is scribed onto a marking surface provided by sticker strip 34 to indicate the position of the index provided by sliding arm 31a. A second vertical reference is thus established to record a vertical position of lower jaw 15a when lower teeth 15, have engaged bite plate 12' relative to the position of upper denture 16' in the patient's closed mouth 14a. The second reference reflects the distance between bite plate 12 and the lower surface of lower jaw 15a.

Bite plate 12' is removed from the patient's mouth 14a and from holding member 19. As described in connection with upper teeth 16, lower surface 12a of bite plate 12' is then coated with impressionable mold-forming material (such as Alginate), to a depth of about 7–8 mm (the height of a tooth). Bite plate 12' is then mounted in holding member 19 and promptly returned to the patient's mouth 14a. Bite plate 12' is situated as disclosed previously with regard to upper denture 16'. The patient next closes the patient's mouth 14a, thereby forcing lower teeth 15 through the impressionable material until the patient's lower teeth 15 contact lower surface 12'a of bite plate 12'. The impressionable material is then allowed to harden. Bite plate 12' is then removed from the patient's mouth 14a and from holding member 19. Bite plate 12' now has on its lower surface 12'a, an open-face mold not unlike mold 23. The open-face mold records and replicates the arrangement and location of lower teeth 15, the mold not here being shown. At this point, lower teeth 15 may be extracted.

Next, a cast-forming material, such as Denta Stone, is poured into the open-faced mold to form mold 23. The cast-forming material is poured to a depth approximating the length of a tooth. The cast-forming material is allowed to flow over the mold onto the lower surface 12'a of bite plate 12', onto anchor nut 12b, and into recess holes 12c. After the cast-forming material has set, forming cast 24, cast 24 is removed from bite plate 12' and all other material is removed from lower surface 12'a. Cast 24 is then reattached to lower surface 12'a of bite plate 12'.

When the patient's lower gums are sufficiently healed, a coating of impressionable material, such as softened wax, is applied to cast 24. Bite plate 12' is again mounted into holding member 19 and reinserted into the patient's mouth 14a, where bite plate 12' is positioned precisely on upper denture 16' and held firmly thereon. At the same time, with registration device 17 positioned as shown in FIG. 7, air cylinder 35 is actuated by an air pressure of about 15 psi. Actuating air cylinder 35 causes shoulder bracket 32b to engage lower jaw 15a and follows its upward movement, as the patient's lower gum is moved upwardly to engage and press against the impressionable material coated onto cast 24. The patient's lower jaw 15a is displaced upwardly until sliding arm 32b reaches previously scribed line 34a. At this point, the excess impressionable material on the cast has been displaced. The cast and the impression made therein are in the same vertical and centric positions as were the natural teeth before extraction.

Air cylinder 35 is shut off when scribed line 34a is reached. Registration device 17 and bite plate 12' mounted thereon are then removed from the patient's mouth 14a. Cast 24 is removed from bite plate 12', having formed a pattern created for the lower denture. This pattern for the lower denture provides a true centric relation with the upper denture and further provides a vertical dimension identical to that of the natural teeth before extraction.

As indicated herein, the upper denture is prepared prior to the lower denture in the making of the patterns herein. Although the procedure herein provides for a complete set of dentures, it is apparent that either an upper or a lower denture may be made with the method and apparatus as herein described. Further adjustment can readily be made for any shrinkage of gums which may occur.

Thus, it can be clearly seen with this pre-extraction device method, a means is provided to create a denture pattern within the mouth 14a of a patient. The denture pattern is created by using the patient's own lower jaw articulation and controlled by establishing pre-extraction references. The pattern will precisely replicate the patient's natural teeth. The vacated roots and the resorbed ridges, now replicated in a cast, have the precision centric relationship and vertical dimension made relative to the newly-healed ridges.

It is well known that resorption begins when new dentures are inserted into the mouth 14a upon healed ridges (gums). Resorption continues throughout the life span of the patient, resulting in a continually changing vertical dimension and in undesirable effects such as an apparent collapsing of the face. To date, there is no known precise method of tracking and determining the extent of a vertical dimension lost due to ridge resorption. However, the vertical dimension is a critical measurement needed when dentures are relined or rebased, if the realigned or rebased dentures are to restore desired facial features and a balanced occlusion.

Figure 10:
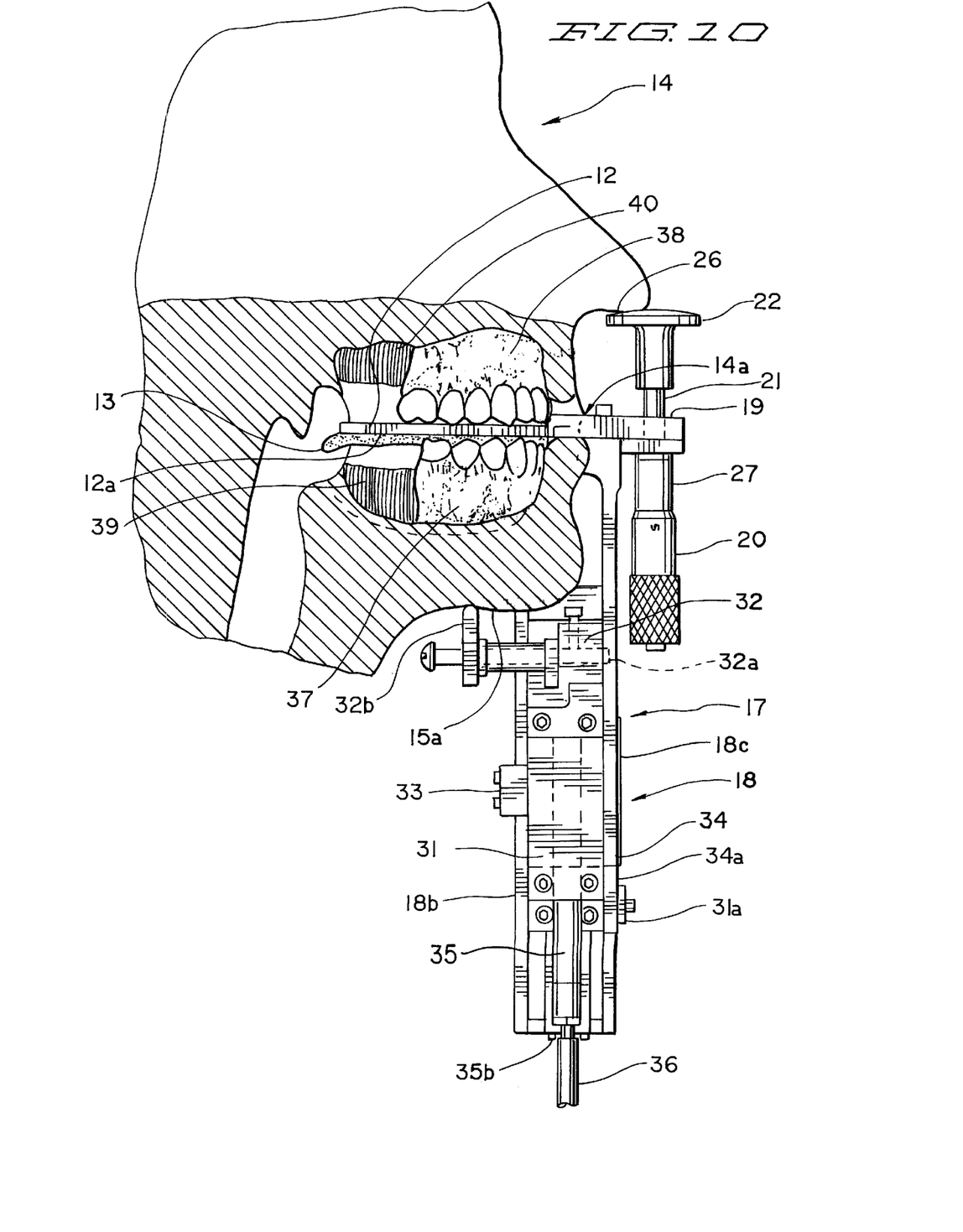
FIG. 10 is a side view of a denture pattern registration device and bite plate in a third operating position.

Thus, another objective is to establish vertical references recording the jaw relationships. The vertical references record the relations of replacement dentures to the patient's healed ridges by means of bite plate 12 positioned between upper denture 38 and lower denture 37 within the patient's mouth 14a (FIG. 10). The purposes of this method are to track and record the progression of ridge resorption and to establish a permanent base line from which subsequent measurements of the resorbing ridge will be taken.

The first step is to apply a layer of an impressionable material 13 to lower surface 12a of bite plate 12. Bite plate 12 is then inserted into the mouth 14a of the patient and positioned over the lower teeth of lower denture 37. The patient then bites down on bite plate 12, causing the lower teeth of denture 37 to bite through layer 13 and contact bite plate 12, thereby creating an impression of the lower teeth of denture 37 in layer 13. The impression present on bite plate 12 has now established a precise location and relationship to the lower teeth of denture 37. Bite plate 12 is then removed from the patient's mouth 14a.

A next step is to establish references between the jaw and bite plate 12 when bite plate 12 is held in the patient's closed mouth 14a. For this purpose, registration device 17 is used. Bite plate 12, with the impression of the lower teeth of denture 37, is attached to holding member 19 and carefully inserted into the patient's mouth 14a, where the impression is positioned over corresponding teeth of denture 37. The patient then closes the patient's mouth 14a on bite plate 12. While thus held, registration device 17 will record a precise relationship between bite plate 12 and new dentures 37, 38 in place on resorbing ridges 39, 40. Measuring the relationship involving upper denture 38 will occur simultaneously, but independently of measuring the relationship involving lower denture 37. For upper denture 38, distance measuring means such as micrometer 20 is used. Micrometer 20 is operated until disc wheel 27 contacts the base 27 of the patient's nose without pressure. The reading 27 on micrometer 20 records a first reference measuring the vertical relation of upper denture 38 to bite plate 12. The micrometer reading 27 is recorded and entered into the patient's record to be compared with in all subsequent examinations for residual resorption of maxillary ridge 40.

Next, while bite plate 12 is still being held upon the patient's mouth 14a, a reference relative to lower denture 37, bite plate 12 is recorded by distance measuring means discussed below. While held, air cylinder 35 is charged with pressurized air, causing rod 35a to extend shoulder bracket 32b upwardly, thereby engaging the bottom side of lower jaw 15a. The air pressure comes from a controlled air supply (not shown), and will continue to rise to a predetermined level, such as 15 psi, at inlet 35b of air cylinder 35. A pressure of 15 psi will cause shoulder bracket 32b to exert one pound of pressure, or less, against the bottom of lower jaw 15a. A line 34a is scribed onto sticker strip 34 to indicate the position of sliding arm 31a. Line 34a is thus a calibrated reference establishing the vertical relation of lower jaw 15a when the lower teeth of denture 37 have engaged bite plate 12 relative to upper teeth of denture 38 in a patient's closed mouth 14a. This reference reflects the distance between bite plate 12 and the bottom surface of jaw 15a.

Bite plate 12 is removed from the patient's mouth 14a and detached from holding member 19. Bite plate 12, along with the established references, may be entered into the patient's records. Bite plate 12 and related references provide the basis from which all future clinical examinations for residual resorption of the patient's ridges may be measured.

The occlusal relationship of the maxilla to the mandible is constantly changing because of the resorbing ridges, often causing the patient's face to appear to collapse. Therefore, after a period of time, the patient may return for a clinical examination of the resorbing ridges, perhaps once a year. The dentist retrieves the patient's records, consisting of bite plate 12 with the impression of the lower teeth of denture 37, the relating reference measurements from micrometer 20, and sticker strip 34.

The dentist reattaches sticker strip 34 and inserts bite plate 12 into holding member 19. Registration device 17 and bite plate 12 are then reinserted into mouth 14a of the patient and positioned as described above. The patient closes the patient's mouth 14a on positioned bite plate 12. A similar procedure will be used to measure a precise relationship between bite plate 12 and the dentures 37, 38 now in place on respective, resorbed ridges 39, 40.

Operating micrometer 20 such that disc wheel 22 engages the base 26 of patient's nose reflects a lesser vertical dimension than the original reference when resorption has occurred. The difference between the reference readings measures the amount of resorption which has occurred since the first measurement.

While registration device 17 and bite plate 12 are still thusly positioned, air cylinder 35 is charged with same controlled air pressure (e.g., 15 psi), thereby actuating shoulder bracket 32b. Shoulder bracket 32b engages the bottom of lower jaw 15a. The new calibrated reference line is scribed on reattached sticker strip 34, proximate formerly scribed line 34a. The pressurized air is then shut off, shoulder bracket 32b drops down from contacting lower jaw 15a, and bite plate 12 is removed from the patient's mouth 14a. Sticker strip 34 is removed from side wall 18c. The distance between the two scribed lines is the measurement of resorption of the mandibular ridge since the first measurement.

It can be clearly seen that, with registration device 17 and the method described, a third function of registering a new bite occlusion and measuring resorption is enabled. The resorption measurements enable the dentures to be precisely relined or rebased, thereby restoring the patient's natural balanced occlusion.

It will, of course, be understood that various changes may be made in the form, details and arrangement of the method and apparatus herein without departing from the scope of the invention such as defined in the appended claims.

What is claimed is:

1. A registration device for creating patterns and determining vertical references for replacement dentures, the dentures conforming to dimensions present in a patient's mouth before tooth extraction, the registration device comprising:

an impressioning member displaying a first surface for accommodating an impressioning material; and a vertical referencing assembly removably attachable to the impressioning member, the vertical referencing assembly comprising means for measuring a vertical relationship between a biting surface on at least one tooth and an anatomical feature of the patient, said vertical measuring means including a marking surface and an index.

2. The registration device of claim 1, the vertical referencing assembly further including a micrometer, the micrometer adjustably positionable proximate a portion of the patient's facial anatomy.

3. The registration device of claim 2, in which the micrometer is positioned so that a portion of the micrometer may be positioned proximate a basal portion of the patient's nose.

4. The registration device of claim 1, the vertical referencing assembly further including a referencing member positionable proximate an anatomical feature, the referencing member operably coupled to a vertical measuring mechanism.

5. The registration device of claim 4, in which the vertical measuring mechanism includes a positioning member generally conformable to a patient's lower jaw and a scribing guide in mechanical communication with the positioning member, the scribing guide and the positioning member cooperating to enable a dimension describing the relationship between a biting surface on at least one tooth and the patient's lower jaw to be measured.

6. A process for registering an oral dimension present in a patient before at least a portion of the patient's teeth are extracted, the process comprising the steps of:

provviding a registration device, the registration device comprising an upper registration assembly, a lower registration assembly and a bite plate, the upper registration assembly accommodating the bite plate, the lower registration assembly operably coupled to the upper registration assembly, the upper and lower registration assemblies including means for measuring a relation between a biting surface on at least one tooth and a base of the patient's nose, a surface of the bite plate accommodating a layer of impressionable material;

making an impression of at least three of the patient's teeth in the layer of impressionable material;

positioning the bite plate with the impressioned layer in the patient's mouth such that the impressioned layer is seated in corresponding teeth, the bite plate being accommodated in the upper registration assembly; and measuring a vertical relationship between the biting surface of at least one of the patient's teeth and the base of the patient's nose by said relation measuring means.

7. The process of claim 6, in which a vertical relationship between a biting surface of at least one of the patient's teeth and the patient's lower jaw is measured.

8. The process of claim 6, in which the impression is made of the patient's upper teeth.

9. The process of claim 6, in which the impression is made of the patient's lower teeth.

10. The process of claim 6, further including the step of making an impression of the patient's gums after the patient's teeth are extracted.

11. The process of claim 10, in which the impression is made of the patient's upper gums.

12. The process of claim 11, in which the impression is made of the patient's lower gums.

13. The process of claim 6, in which said impression has been made in teeth present in replacement dentures and in which the measured vertical relationship is compared to an earlier vertical relationship to determine how the replacement dentures will be redimensioned to better fit the patient.

* * * * *